(12) United States Patent
Kakiuchi

(10) Patent No.: US 8,684,977 B2
(45) Date of Patent: Apr. 1, 2014

(54) COMBINED CONTAINER-SYRINGE

(75) Inventor: Makoto Kakiuchi, Ibaraki-ken (JP)

(73) Assignee: Arte Corporation, Tokyo (JP)

( * ) Notice: Subject to any disclaimer, the term of this patent is extended or adjusted under 35 U.S.C. 154(b) by 464 days.

(21) Appl. No.: 12/430,849

(22) Filed: Apr. 27, 2009

(65) Prior Publication Data
US 2010/0198164 A1   Aug. 5, 2010

(30) Foreign Application Priority Data

Jan. 30, 2009   (JP) ................. 2009-020858

(51) Int. Cl.
*A61M 5/32* (2006.01)

(52) U.S. Cl.
USPC .......................... 604/198; 604/197

(58) Field of Classification Search
USPC ........... 604/263, 110, 192, 198, 197
See application file for complete search history.

(56) References Cited

U.S. PATENT DOCUMENTS

| | | | |
|---|---|---|---|
| 2,409,656 A | 10/1946 | Austin | |
| 2,627,757 A | 2/1953 | Austin | |
| 5,269,766 A | 12/1993 | Haber et al. | |
| 5,290,256 A | 3/1994 | Weatherford et al. | |
| 5,376,080 A | 12/1994 | Petrussa | |
| 5,433,712 A | 7/1995 | Stiles et al. | |
| 5,562,626 A | 10/1996 | Sanpietro | |
| 5,591,138 A * | 1/1997 | Vaillancourt | 604/263 |
| 6,149,630 A | 11/2000 | Robinson | |
| 6,319,234 B1 | 11/2001 | Restelli et al. | |
| 6,852,096 B1 | 2/2005 | Pouget et al. | |
| 7,211,065 B2 * | 5/2007 | Miller | 604/110 |
| 7,300,421 B1 | 11/2007 | Lowry et al. | |
| 2003/0229314 A1 | 12/2003 | McWethy et al. | |
| 2004/0122379 A1 * | 6/2004 | Bosse et al. | 604/263 |
| 2007/0179441 A1 | 8/2007 | Chevallier | |

FOREIGN PATENT DOCUMENTS

| | | |
|---|---|---|
| EP | 1362609 A1 | 11/2003 |
| EP | 2 022 523 A1 | 2/2009 |
| EP | 2 022 523 A1 | 11/2009 |
| FR | 2 799 975 A1 | 4/2001 |
| JP | 09-225030 A | 9/1997 |

(Continued)

OTHER PUBLICATIONS

European Search Report for Application No. EP 09 15 8842 mailed Oct. 6, 2011.

(Continued)

*Primary Examiner* — Bhisma Mehta
*Assistant Examiner* — Brandy S Lee
(74) *Attorney, Agent, or Firm* — Nixon Peabody LLP

(57) ABSTRACT

A combined container-syringe includes a body that has an outer tube to be filled with a drug solution. A cylindrical tip is attached to a front end portion of the outer tube and to a front end portion of which an injection needle is attached. A cylindrical safety device is attached on an outer circumferential surface of the outer tube in a freely sliding manner. A first retaining member fixes the safety device in a disengageable manner at a first position where the safety device is separated from the injection needle. A second retaining member fixes the safety device at a second position where the safety device covers the injection needle. A biasing member biases the safety device in the direction from the first position to the second position. A latch releasing member releases the engagement by the first retaining member.

5 Claims, 16 Drawing Sheets

(56) References Cited

FOREIGN PATENT DOCUMENTS

| | | |
|---|---|---|
| JP | 11-169360 | 6/1999 |
| WO | 01/85239 A2 | 11/2001 |
| WO | 2006/008086 A1 | 1/2006 |

OTHER PUBLICATIONS

Japanese Office Action in Japanese Application No. 2009-142652, mailed on Mar. 26, 2013.

* cited by examiner

COMBINED CONTAINER-SYRINGE

CROSS REFERENCE TO RELATED APPLICATIONS OR PRIORITY CLAIM

Priority is claimed on Japanese Patent Application No. 2009-020858, filed Jan. 30, 2009, the content of which is incorporated herein by reference.

BACKGROUND OF THE INVENTION

1. Field of the Invention

The present invention relates to a combined container-syringe that is provided with a safety device that is used for covering the injection needle after the completion of injection and the like and ensuring safety.

2. Description of the Related Art

A combined container-syringe can be used immediately after being removed from the packaging without performing troublesome procedures at medical institutions due to the fact that the drug solution has been prefilled. Therefore, it is very convenient and useful in terms of reducing the workload on those working in the medical industry, such as physicians and nurses. For this reason, it is being adopted by many medical facilities.

When syringes are used by those in the medical industry, they have to pay attention to the treatment of the syringes so as not to accidentally inject themselves with the needle after use. For that reason, with the aim of safely processing needles after injection, a syringe has been proposed that is equipped with a safety device in the form of a cylindrical cover that prevents careless contact with the needle by covering the injection needle therewith after injection.

For example, according to the syringe that is disclosed in Japanese Unexamined Patent Application, First Publication No. 2001-29334, a safety device having flexibility is engaged on an outer circumferential surface of a cylinder, and by applying pressure to the safety device to be flexed, the engagement state is released. By pointing the injection needle upward while holding the syringe by the safety device, the syringe body moves downward by its own weight, whereby the injection needle becomes covered with the safety device.

However, in the syringe that is equipped with a conventional safety device as described above, the means that causes the safety device to move to a position that covers the needle is merely the syringe body's own weight. Due to this fact, the force of relative movement of the safety device with respect to the needle is weak, and depending on the circumstances the safety device may become caught on the syringe body in the middle of covering the injection needle. As a result, the syringe that is equipped with the conventional safety device suffers from problems because the safety device is not able to reliably cover the injection needle, whereby not ensuring safety.

The safety device may be manually moved. However, in this case, both hands have to be used such that the safety device is moved with one hand while holding the syringe body with the other hand. Therefore, since the operation requires both hands, it is complicated.

Furthermore, in the syringe that is equipped with a conventional safety device as described above, the safety device is attached to the syringe body only by friction with an engagement portion. Due to this fact, the safety device is not strongly fixed to the syringe body and the safety device is relatively easy to become removed from the syringe body. As a result, there is a problem that people involved in medical services have to pay attention to treatment of the syringes. Furthermore, it is desirable that the safety device be easily attached to a conventional syringe body.

The present invention was achieved in view of the above circumstances, and has as an object to provide a combined container-syringe that can ensure safety by reliably causing the safety device to move with respect to the syringe body to a state of covering the injection needle.

The present invention also has as an object to provide a combined container-syringe that is equipped with a safety device that can be easily attached to a syringe body and can be reliably fixed to the syringe body in a state where the safety body covers the injection needle after the completion of injection.

SUMMARY OF THE INVENTION

In order to solve the abovementioned problem, this invention proposes the following means.

According to an aspect of the invention, a combined container-syringe includes: a combined container-syringe body that has an outer tube inside of which a drug solution is filled, a cylindrical tip which is attached to a front end portion of the outer tube and to a front end portion of which an injection needle is attached, and a finger grip that is attached to a rear end portion of the outer tube; a cylindrical safety device which is attached on an outer circumferential surface of the outer tube in a freely sliding manner; a first retaining member that fixes the safety device in a disengageable manner at a first position where the safety device is separated from the injection needle; a second retaining member that fixes the safety device at a second position where the safety device covers the injection needle; a biasing member that biases the safety device in the direction from the first position to the second position; and a latch releasing member that releases the engagement by the first retaining member.

According to this combined container-syringe, when the engagement of the safety device at the first position by the first retaining member is released by the latch releasing member, the safety device moves to the second position by the biasing force of the biasing member and is engaged at the second position by the second retaining member. Accordingly, it is possible to reliably move the safety device to a position where the injection needle is covered with the safety device only by operating the latch releasing member.

In the combined container-syringe according to the invention, the finger grip may have a cylindrical fitting portion that is attached to the rear end portion of the outer tube, and a flange surface that protrudes outward in a radial direction of the combined container-syringe body from an outer circumferential surface of a rear end portion of the fitting portion and faces backward; the first retaining member may have an engagement portion that is provided in a rear end portion of the safety device and a latch portion that is provided on the outer circumferential surface of the fitting portion and is engaged with the engagement portion; the latch releasing member may be a slide member that is capable of sliding on the flange surface along the radial direction of the combined container-syringe body from a waiting position where the slide member is disposed at a position closer to the outside in the radial direction of the combined container-syringe body to a releasing position where the slide member is disposed at a position closer to the inside in the radial direction of the combined container-syringe body; and the slide member may release the engagement of the latch portion with the engagement portion when the slide member slides from the waiting position to the releasing position.

In this case, by moving the slide member disposed on the flange surface of the finger grip from the waiting position to the releasing position, the slide member releases the engagement between the latch portion of the fitting portion of the finger grip and the engagement portion of the rear end portion of the safety device. Thereby, the safety device moves to the second position by the biasing force of the biasing member and is engaged at the second position by the second retaining member. Accordingly, since the safety device moves to the second position only by sliding the slide member, it is possible to easily and reliably cover the injection needle with the safety device to ensure safety.

In the combined container-syringe according to the invention, the engagement portion may protrude parallel to an axis of the combined container-syringe body from the rear end portion of the safety device and may be elastically deformable in the radial direction of the combined container-syringe body; the slide member may have a sloping side surface that slopes inward in the radial direction of the combined container-syringe body from the waiting position side to the releasing position side and is capable of abutting an inner surface of the engagement portion; and the sloping side surface may press the engagement portion such that the engagement portion is elastically deformed outward in the radial direction of the combined container-syringe body when the slide member moves to the releasing position.

In this case, when the slide member moves from the waiting position to the releasing position, the sloping side surface presses the engagement portion of the safety device, which is engaged with the latch portion of the fitting portion, outward in the radial direction of the combined container-syringe body so that the engagement portion is separated from the latch portion. Thereby, the engagement between the engagement portion and the latch portion is released. Accordingly, it is possible to reliably move the safety device to the second position by sliding the slide member.

In the combined container-syringe according to the invention, the combined container-syringe may further include a plunger rod which extends along the axis of the combined container-syringe body, is inserted into the outer tube from the rear end side, and is pushed forward at the time of injection; the slide member may have a penetrating portion having a larger-diameter hole that penetrates the slide member along the axis when the slide member is positioned at the waiting position, and a smaller-diameter slit that penetrates the slide member along the axis when the slide member is positioned at the waiting position, extends along a direction to which the sliding member slides, and is connected with the larger-diameter hole; the plunger rod may have a larger-diameter rod portion that is capable of being inserted into the larger-diameter hole but is not capable of being inserted into the smaller-diameter slit, and a smaller-diameter rod portion that is capable of being inserted into the larger-diameter hole and the smaller-diameter slit; the larger-diameter rod portion may be inserted through the penetrating portion before injection when the plunger rod is positioned at the most rear end side and at the time of injection when the plunger rod is pushed forward; and the smaller-diameter rod portion may be inserted through the penetrating portion after completion of injection when the plunger rod is pushed to the most front end side.

In this case, before injection and at the time of injection, the larger-diameter rod portion of the plunger rod is inserted through the larger-diameter hole of the penetrating portion. In this state, the larger-diameter rod portion cannot be inserted through the smaller-diameter slit. Accordingly, even when a user attempts to slide the slide member from the waiting position to the releasing position, sliding movement of the slide member is prevented by the larger-diameter rod portion.

On the other hand, after completion of injection, the smaller-diameter rod portion of the plunger rod is inserted through the larger-diameter hole of the penetrating portion. In this state, when a user attempts to slide the slide member from the waiting position to the releasing position, the smaller-diameter rod portion enters the smaller-diameter slit from the larger-diameter hole so that the smaller-diameter rod portion is inserted through the smaller-diameter slit. Accordingly, the smaller-diameter rod portion does not prevent the sliding movement of the slide member.

Therefore, since the slide member can slide from the waiting position to the releasing position only after the completion of injection, it is possible to reliably prevent accidental movement of the safety device before and at the time of injection.

In the combined container-syringe according to the invention, the second retaining member may have a device engagement portion that is formed by a part of the cylindrical tip expanding in diameter, and has a front engagement surface facing forward and a rear engagement surface facing backward, a return prevention stopper that protrudes from an inner circumferential surface of the safety device, and is engaged with the front engagement surface when the safety device is positioned at the second position so as to prevent movement of the safety device toward the rear end, and a slip-out prevention stopper that protrudes from the inner circumferential surface of the safety device at a position closer to the rear end than the slip-out prevention stopper, and is engaged with the rear engagement surface when the safety device is positioned at the second position so as to prevent movement of the safety device toward the front end.

In this case, when the safety device is positioned at the second position, the return prevention stopper is engaged with the front engagement surface of the device engagement portion so as to prevent movement of the safety device toward the rear end. Furthermore, the slip-out prevention stopper is engaged with the rear engagement surface of the device engagement portion so as to prevent movement of the safety device toward the front end.

That is, since movement of the safety device at the second position in the axis direction is prevented, the safety device does not separate from the combined container-syringe body, and neither does it move in the direction of the rear end and cause the injection needle to be exposed.

In the combined container-syringe according to the invention, the return prevention stopper may slope inward in the radial direction of the combined container-syringe body toward the rear end and the slip-out prevention stopper slopes inward in the radial direction of the combined container-syringe body toward the front end.

In this case, it is possible to easily attach the safety device on the outer circumferential surface of the combined container-syringe body, and it is possible to reliably fix the safety device to the position where the injection needle is covered with the safety device.

In the combined container-syringe according to the invention, the slip-out prevention stopper may slope inward in the radial direction of the combined container-syringe body toward the front end; the return prevention stopper may be elastically deformable in the radial direction of the combined container-syringe body; a pressing ring may be fitted on an outer circumferential surface of the safety device in a freely sliding manner; and the return prevention stopper may protrude from the inner circumferential surface of the safety device by sliding the pressing ring to the position of the return prevention stopper such that the pressing ring presses the return prevention stopper inward in the radial direction of the combined container-syringe body.

In this case, the safety device is mounted on the outer circumferential surface of the combined container-syringe body from the front end side, since the sloping surface of the slip-out prevention stopper abuts the front engagement surface so that the inner circumferential surface of the safety device is flexed, and the slip-out prevention stopper easily passes over the device engagement portion.

Moreover, the return prevention stopper that does not normally protrude inward in the radial direction protrudes inward in the radial direction only when pressing from the outside by the pressing ring.

Accordingly, when the safety device is mounted on the outer circumferential surface of the outer tube from the front end side, it is possible to prevent the return prevention stopper from abutting the device engagement portion by preventing the return prevention stopper from protruding inward in the radial direction. As a result, it is possible to easily mount the safety device without the return prevention stopper preventing the movement of the safety device.

In the combined container-syringe according to the invention, the safety device may have a spring receiving portion that is formed on the inner circumferential surface of the rear end portion thereof; the biasing member may be a coil spring; and, in a state of the safety device being fixed at the first position, the coil spring may be mounted in a compressed state between the spring receiving portion and the finger grip.

In this case, when the engagement of the safety device at the first position by the first retaining member is released, the coil spring, which is mounted in a compressed state between the spring receiving portion that is formed on the inner circumferential surface of the rear end portion of the safety device and the finger grip that is fixed to the rear end portion of the combined container-syringe body, expands forward with respect to the finger grip so that the safety device moves toward the front end. Accordingly, it is possible to reliably move the safety device to the second position where the injection needle is covered with the safety device.

DETAILED DESCRIPTION OF THE INVENTION

An embodiment of the combined container-syringe according to the invention will be described hereinbelow with reference to drawings.

Figure 1:
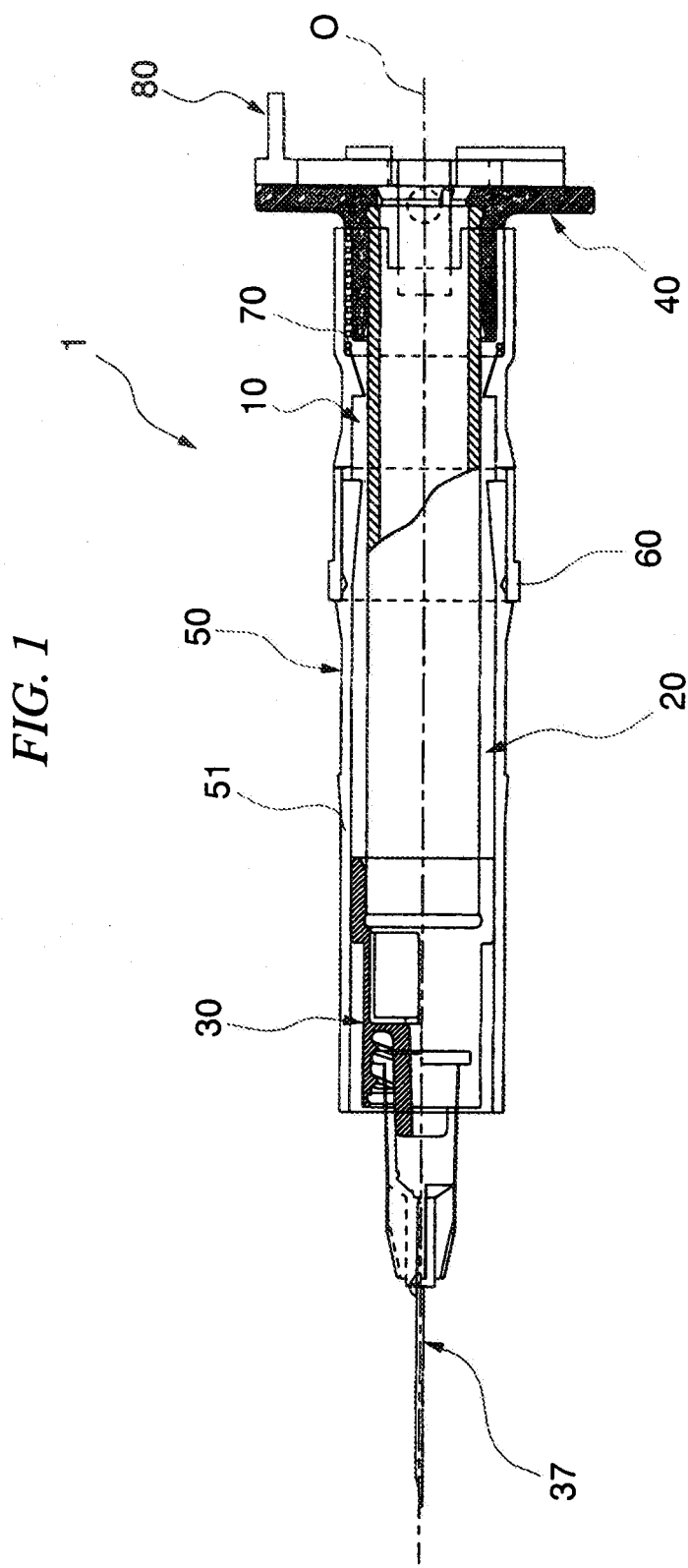
FIG. 1 is a side view showing a partial cross-section of a combined container-syringe according to an embodiment of the invention.

As shown in FIG. 1, a combined container-syringe 1 in this embodiment includes a combined container-syringe body 10 which extends along an axis O and a safety device 50 which is attached to the combined container-syringe body 10. An injection needle 37 is attached to the combined container-syringe body 10. The combined container-syringe 1 includes a first retaining member that a first retaining member that engages the safety device 50 in a disengageable manner at a first position where the safety device 50 is separated from the injection needle 37; a second retaining member that engages the safety device 50 at a second position where the safety device 50 covers the injection needle 37; a coil spring (biasing member) 70 that biases the safety device 50 in the direction from the first position to the second position; and a slide member (latch releasing member) 80 that releases the engagement by the first retaining member.

Hereinbelow, a radial direction of the combined container-syringe body 10 is called merely "the radial direction", a side to which the injection needle 37 is provided in the combined container-syringe body 10 is called "front end side" or "forward", and a side to which a finger grip 40 is provided in the combined container-syringe body 10 is called "rear end side" or "backward".

Figure 2:
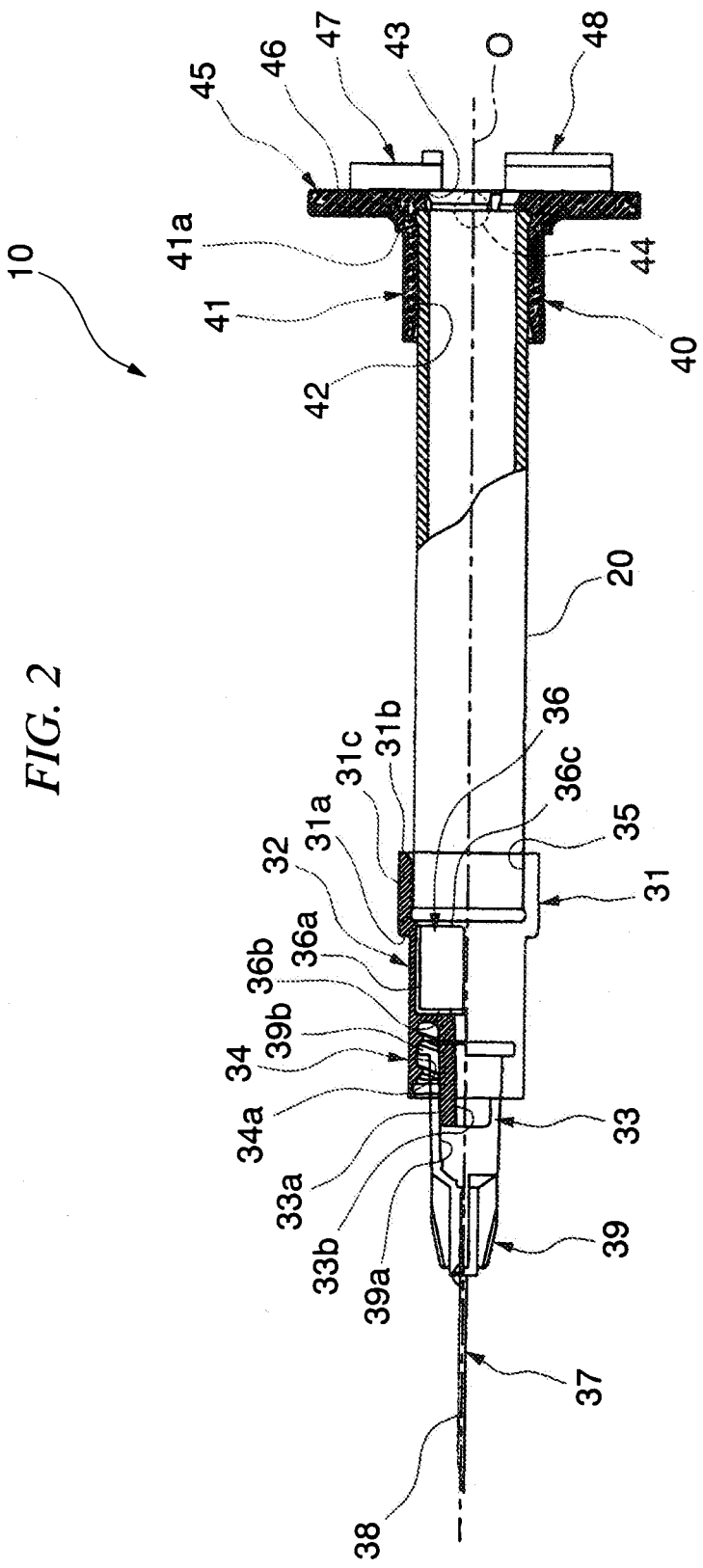
FIG. 2 is a side view showing a partial cross-section of a combined container-syringe body according to the embodiment of the invention.

As shown in FIG. 2, the combined container-syringe body 10 includes an outer tube 20, a hub-luer lock (cylindrical tip) 30 that is attached to the front end portion (left side in FIG. 2) of the outer tube 20 and to the front end of which the injection needle 37 is attached, and the finger grip 40 that is attached to the rear end portion (right side in FIG. 2) of the outer tube 20.

The outer tube 20 is made of transparent material such as glass and synthetic resin, and has a cylindrical shape that extends along the axis O. Drug solution (not shown in the drawings) is filled inside the outer tube 20. The drug solution is sealed from the rear end side by a stopper (not shown in the drawings) provided in the outer tube 20 in a liquid-tight manner.

The hub-luer lock 30 is made of transparent synthetic resin having moderate rigidity. The hub-luer lock 30 has a cylindrical shape with the axis O serving as a center line and a plurality of steps are formed on the outer circumferential surface thereof. The hub-luer lock 30 includes a cylindrical device engagement portion 31, a cylinder portion 32, a luer tip 33, and a cylindrical luer lock portion 34. The cylinder portion 32 is connected to the front end portion of the device engagement portion 31 in a state where the cylinder portion 32 is reduced in diameter than the device engagement portion 31 so as to form a step therebetween. The luer tip 33 is connected to the front end portion of the cylinder portion 32 in a state where the luer tip 33 is reduced in diameter than the cylinder portion 32 so as to form a step therebetween. The luer lock portion 34 is provided outside the luer tip 33 so as to form a gap therebetween and is connected to the front end portion of the cylinder portion 32.

The rear end portion of the device engagement portion 31 is opened backward so as to form a fitting hole 35 into which the front end portion of the outer tube 20 is inserted and fitted. As a result, the hub-luer lock 30 is strongly fixed to the front end portion of the outer tube 20. An end surface of the device engagement portion 31 that faces forward (that is, a step portion between the device engagement portion 31 and the cylinder portion 32) serves as a front engagement surface 31a, and an end surface of the device engagement portion 31 that faces backward serves as a rear engagement surface 31b. The device engagement portion 31 includes an outer circumferential surface 31c which has a cylindrical shape with the axis O serving as a center line, and the front and rear engagement surfaces 31a and 31b are orthogonal to the outer circumferential surface 31c.

A cylindrical bypass chamber 36 having a bottom portion 36b is formed in a portion of the device engagement portion 31 which is positioned closer to the front end than the fitting hole 35, that is, inside the cylinder portion 32. The inner diameter of the bypass chamber 36 is smaller than the diameter of the fitting hole 35. A plurality of bypass grooves 36a which extend along the axis O are formed on the inner circumferential wall of the bypass chamber 36 such that the bypass grooves 36a are uniformly spaced in the circumferential direction. The bypass grooves 36a extend to the center of the bottom portion 36b of the bypass chamber. An annular groove 36c with the axis O serving as a center is formed at the boundary between the bypass chamber 36 and the fitting hole 35. The rear ends of the bypass grooves 36a are connected to each other by the annular groove 36c.

An outer circumferential surface 33a of the luer tip 33 has a tapered shape gradually reducing the diameter toward the front end. A connection hole 33b is provided inside the luer tip 33 so that the connection hole 33b penetrates the luer tip 33 along the axis O and is connected to the center of the bottom portion 36b of the bypass chamber 36.

A lock screw 34a for locking a needle base 39 of the injection needle 37 is formed on the inner circumferential surface of the luer lock portion 34.

The injection needle 37 includes an injection needle body 38 that extends toward the front end along the axis O and the needle base 39 that is provided in the rear end portion of the injection needle body 38. A taper hole 39a that is centered at the axis O and gradually reduces the diameter toward the front end in the rear end portion of the needle base 39. A screwing protrusion 39b that protrudes outward in the radial direction is formed in the rear end portion of the needle base 39. The taper hole 39a of the luer tip 33 is fitted to the taper-shaped outer circumferential surface 33a of the luer tip 33 and the screwing protrusion 39b is screwed to the lock screw 34a of the luer lock portion 34. As a result, the injection needle 37 is strongly fixed to the front end portion of the hub-luer lock 30.

Figure 3:
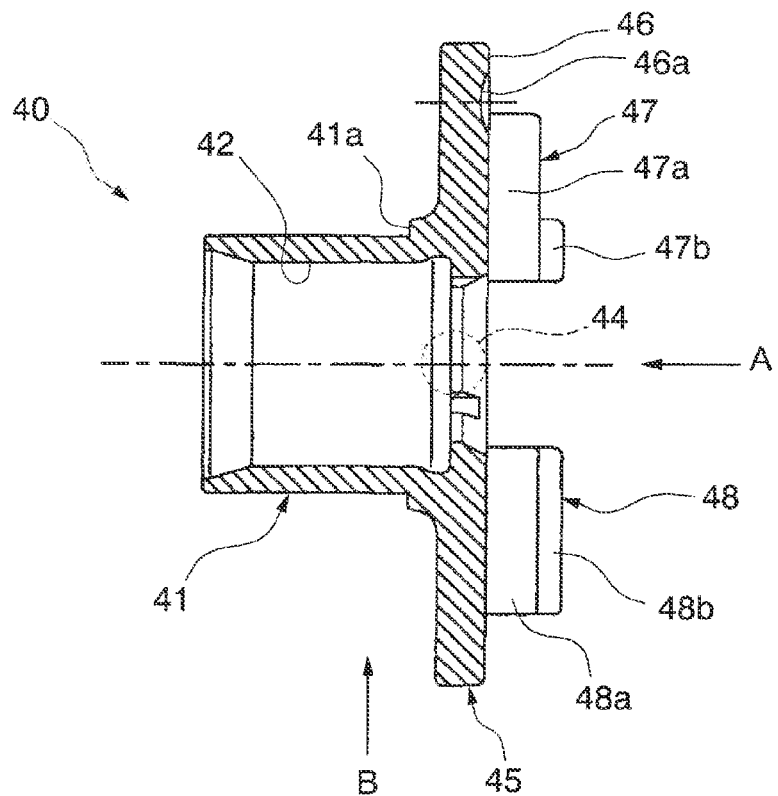
FIG. 3 is a side sectional view of a finger grip according to the embodiment of the invention.
Figure 4:
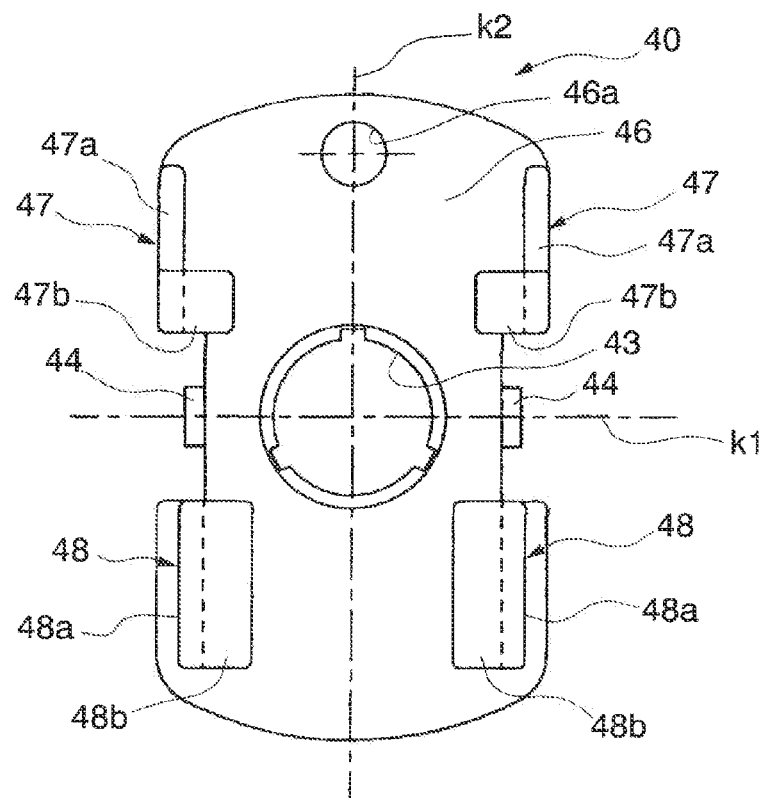
FIG. 4 is a view seen from arrow A in FIG. 3.

As shown in FIGS. 3 and 4, the finger grip 40 includes a cylindrical fitting portion 41 and a flange portion 45 that protrudes outward in the radial direction from the rear end portion of the fitting portion 41.

A fitting hole 42 into which the rear end portion of the outer tube 20 is fitted is provided inside the fitting portion 41. The rear end portion of the fitting portion 41 is opened backward so as to form an insertion hole 43 having a diameter smaller than the fitting portion 41.

A pair of cylindrical latch protrusion portions (latch portions) 44, 44 that protrude outward in the radial direction are formed on the outer circumferential surface of the fitting portion 41. The latch protrusion portions 44, 44 are disposed at the same position in the axis O direction and spaced by 180° in the circumferential direction.

A spring abutting step portion 41a having an annular shape centered at the axis O is formed on the outer circumferential surface of the fitting portion 41. The spring abutting step portion 41a faces forward and is positioned directly on the front end side of the latch protrusion portions 44, 44. The rear end portion of the coil spring 70 abuts the spring abutting step portion 41a.

The flange portion 45 has a substantially rectangular shape such that, when seen from the rear end, short sides of the flange portion 45 are parallel to a line k1 which passes the latch protrusion portions 44, 44 and long sides of the flange portion 45 are parallel to a line k2 which is orthogonal to the line k1 and the axis O. A surface of the flange portion 45 which faces backward serves as a flat flange surface 46 and the insertion hole 43 having a circular cross section is provided in the center of the flange surface 46.

As shown in FIG. 4, a pair of first guide portions 47, 47 are provided on the flange surface 46 so as to separate with each other by a predetermined distance with the line k2 serving as a center line. The pair of first guide portions 47, 47 are positioned in one portion of the flange portion 45 of two portions into which the flange portion 45 is divided with the line k1 serving as a boundary line (upper portion of the two portions in FIGS. 3 and 4). Each of the first guide portions 47, 47 is provided with a side guide 47a and an upper guide 47b. The side guides 47a, 47a protrude from the flange surface 46 so as to be orthogonal to the flange surface 46 and extend along the line k2. The upper guides 47b, 47b extend from edges of the side guides 47a closer to the line k1 (that is, edges closer to the latch protrusion portions 44, 44 when seen from the rear end) such that the upper guides approach to each other (that is, extend toward the line k2).

An latch recess portion 46a which is depressed in a hemispherical shape is formed in the one portion of the flange surface 46. The latch recess portion 46a is positioned at a position on the line k2 and near the edge of the flange surface 46 (that is, in the upper side in FIG. 4).

Figure 5:
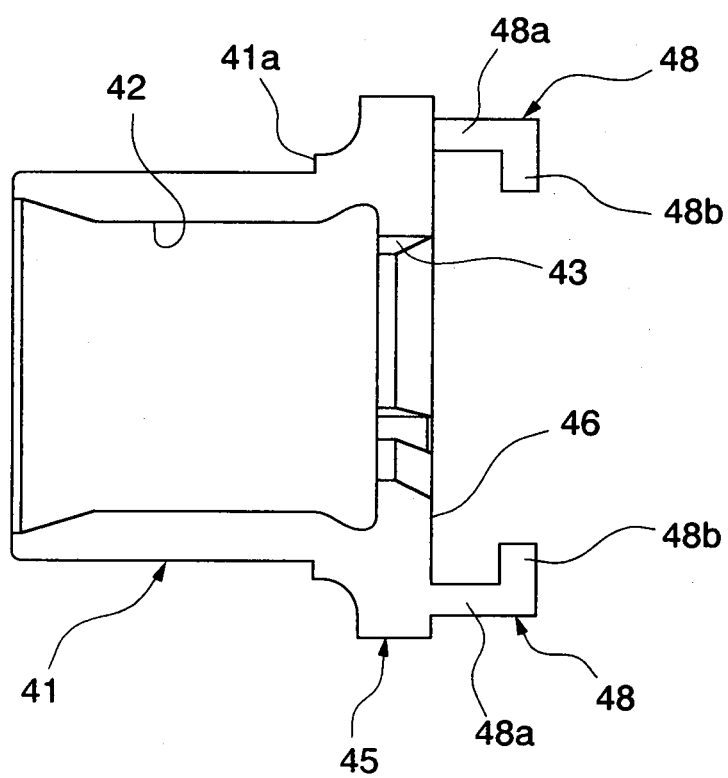
FIG. 5 is a view seen from arrow B in FIG. 3.

A pair of substantially L-shaped second guide portions 48, 48 are provided on the flange surface 46 so as to separate with each other by a predetermined distance with the line k2 serving as a center line. The pair of second guide portions 48, 48 are positioned in the other portion of the flange portion 45 of two portions into which the flange portion 45 is divided with the line k1 serving as a boundary line (lower portion of the two portions in FIGS. 3 and 4). As shown in FIGS. 3 to 5, each of the second guide portions 48, 48 is provided with a side guide 48a and an upper guide 48b. The side guides 48a, 48a protrude from the flange surface 46 so as to be orthogonal to the flange surface 46 and extend along the line k2. The upper guides 48b, 48b extend from upper edges of the side guides 48, 48 such that the upper guides approach to each other (that is, extend toward the line k2). The distance between the second guide portions 48, 48 is smaller than the distance between the first guide portions 47, 47.

Figure 6:
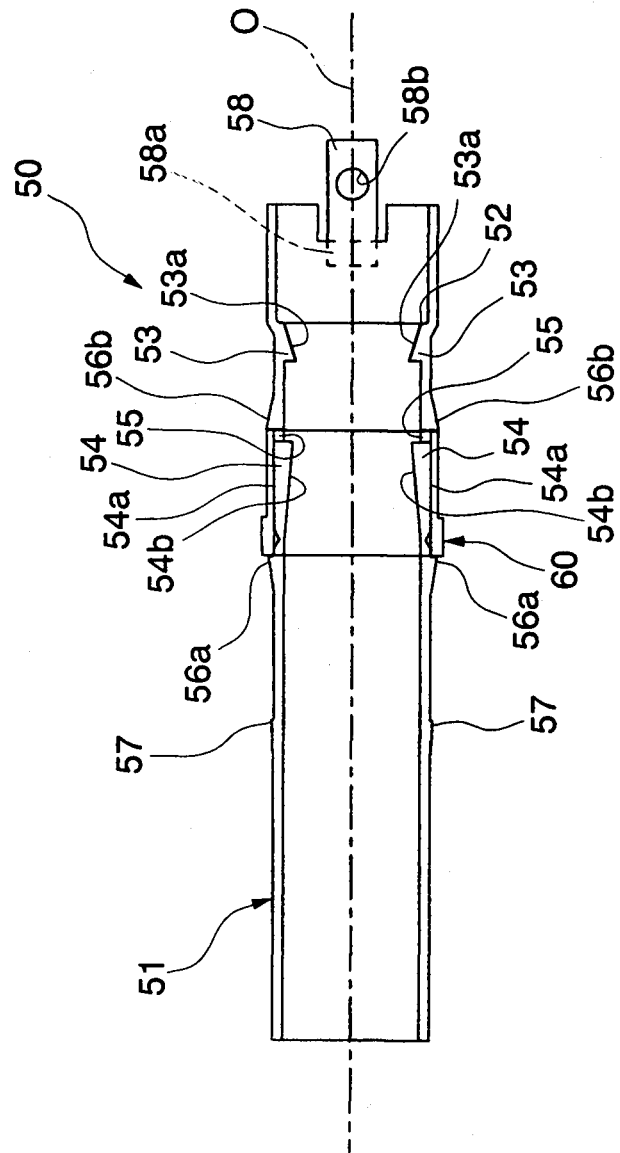
FIG. 6 is a side view of a safety device according to the embodiment of the invention in a state where return prevention stoppers are pressed by a pressing ring.
Figure 7:
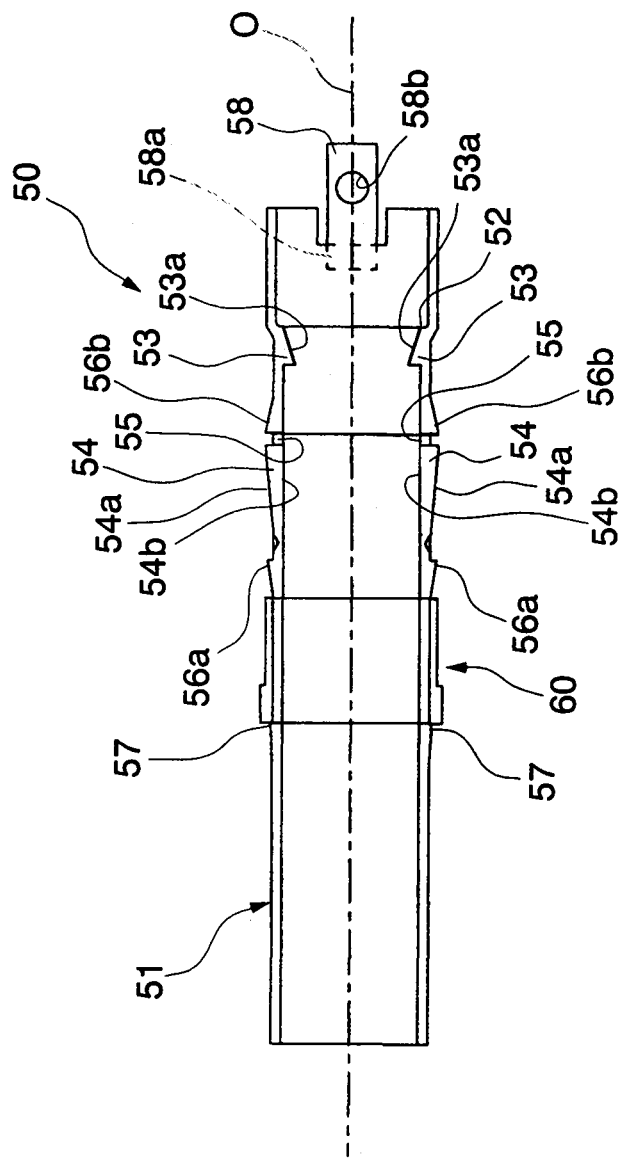
FIG. 7 is a side view of the safety device according to the embodiment of the invention in a state where the return prevention stoppers are not pressed by the pressing ring.
Figure 8:
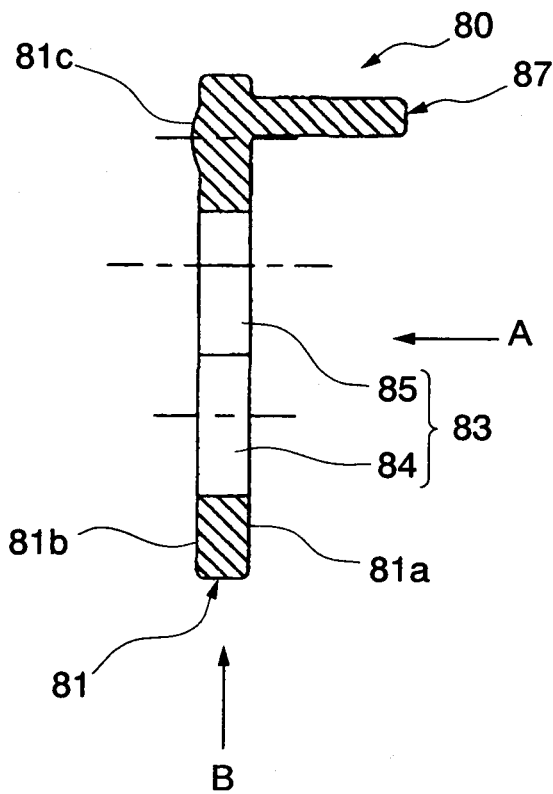
FIG. 8 is a side sectional view of a slide member according to the embodiment of the invention.

The safety device 50 is attached on the outer circumferential surface of the combined container-syringe body 10 having the above-described structure. As shown in FIGS. 1, 6 and 7, the safety device 50 includes a safety device body 51 and a pressing ring 60.

The safety device body 51 is made with a material that is transparent and has moderate flexibility such as polypropylene and thinly fabricated in a range that can maintain strength. As shown in FIGS. 6 and 7, the safety device body 51 has a substantially cylindrical shape with the axis O serving as a center line. The inner diameter of the safety device body 51 is substantially equal to the outer diameter of the outer circumferential surface 31c of the device engagement portion 31.

The rear end portion (enlarged portion) of the safety device body 51 is enlarged in diameter so as to form a step portion. A surface that is provided inside this step portion and faces backward serves as a spring receiving portion 52 against which the distal end portion of the coil spring 70 is abutted.

A plurality of slip-out prevention stoppers 53 are provided in the safety device body 51 directly on the front end side of the spring receiving portion 52 so as to be uniformly spaced in the circumferential direction. Each of the slip-out prevention stoppers 53 protrudes inward in the radial direction so as to form a sloping surface 53a that slopes inward in the radial direction toward the front end.

Moreover, a plurality of return prevention stoppers 54 are provided in the safety device body 51 closer to the distal end than the slip-out prevention stoppers 53. When pressed inward in the radial direction by the pressing ring 60, the return prevention stoppers 54 protrude inward in the radial direction from the inner circumferential surface. In this embodiment, positions of the slip-out prevention stoppers 53 in the circumferential direction are coincident with those of the return prevention stoppers 54. However, positions of the slip-out prevention stoppers 53 in the circumferential direction may be different from those of the return prevention stoppers 54.

As described above, when pressed inward in the radial direction by the pressing ring 60, the return prevention stoppers 54 protrude inward in the radial direction from the inner circumferential surface. Hereinafter, a state shown in FIG. 6 where the return prevention stoppers 54 are pressed by the pressing ring 60 is referred to as "pressing state", and a state shown in FIG. 7 where the return prevention stoppers 54 are not pressed by the pressing ring 60 is referred to as "non-pressing state". The return prevention stopper 54 is surrounded on the rear end side and both sides in the circumferential direction by a U-shaped slit 55. By this U-shaped slit 55, the return prevention stopper 54 is flexed in the radial direction in the manner of a flat spring. In the non-pressing state, the outer circumferential surface of the return prevention stopper 54 serves as a pressed surface 54a that slopes outward in the radial direction toward the rear end. When the pressed surface 54a is pressed inward in the radial direction by the pressing ring 60, the inner circumferential surface of the return prevention stopper 54 forms a sloping surface 54b that slopes inward in the radial direction toward the rear end.

The slip-out prevention stopper 53 and the return prevention stopper 54 constitute the second retaining member that fixes the safety device 50 at the second position where the safety device 50 moves forward and covers the injection needle 37.

A pair of ring secondary stop projections 56a, 56b are provided in front of and behind the return prevention stopper 54, respectively, so as to sandwich the return prevention stopper 54 from the front end side and the rear end side.

The ring secondary stop projection 56a that is positioned at the front end side slopes outward in the radial direction toward the rear end, and the ring secondary stop projection 56b that is positioned at the rear end side slopes outward in the radial direction toward the front end.

Also, a plurality of ring primary stop projections 57 that project outward in the radial direction are provided so as to be uniformly spaced in the circumferential direction, being positioned closer to the front end than the front end side ring secondary stop projection 56a.

As shown in FIGS. 6 and 7, the pressing ring 60 that is fitted on the safety device body 51 has a cylindrical shape in which the length in the axis O direction is sufficiently shorter than the safety device body 51, and the pressing ring 60 is made with a material that is transparent and has moderate flexibility such as polypropylene and thinly fabricated in a range that can maintain strength. The inner diameter of the pressing ring 60 is substantially equal to the outer diameter of the outer circumferential surface of the safety device body 51. Thereby, the pressing ring 60 can slide on the outer circumferential surface of the safety device body 51 along the axis O.

In the non-pressing state, as shown in FIG. 7, the pressing ring 60 is positioned directly on the rear end side of the ring primary stop projection 57. The pressing ring 60 is fixed by the ring primary stop projections 57 so as not to move forward. Also, in this state, the rear end of the pressing ring 60 abuts the sloping surface of the front end side ring secondary stop projection 56a. Thereby, the pressing ring 60 is locked so as not to accidentally move backward.

When pressing the return prevention stopper 54 by the pressing ring 60, the pressing ring 60 is relatively moved backward with respect to the safety device body 51. In this case, by applying force sufficient to move the pressing ring 60, the inner circumferential surface of the pressing ring 60 passes over the sloping surface of the front end side ring secondary stop projection 56a and the pressing ring 60 is moved backward.

After the pressing ring 60 passes over the ring secondary stop projection 56a thus, the inner circumferential surface of the pressing ring 60 presses the pressed surface 54a of the return prevention stopper 54. Thereby, as shown in FIG. 6, the return prevention stoppers 54 protrude inward in the radial direction. In this case, since the front end portion and the rear end portion of the pressing ring 60 abut the ring secondary stop projections 56a and 56b, respectively, movement of the pressing ring 60 in the axis O direction is stopped.

A pair of engagement plates (engagement portions) 58, 58 are provided on the safety device body 51 such that the engagement plates 58, 58 extend backward form the rear end portion of the safety device body 51 along the axis O. The engagement plates 58, 58 are parallel to each other and oppose to each other so as to be spaced by 180° in the circumferential direction. The engagement plate 58 is connected to the outer circumferential surface of the safety device body 51 at a connection portion 58a, and is elastically deformable in the radial direction with the connection portion 58a serving as a fulcrum point. The engagement plate 58 is provided with a circular engagement hole 58b that penetrates the engagement plate 58 in the thickness direction (the radial direction) thereof. The inner diameter of the engagement hole 58b is substantially equal to the outer diameter of the latch protrusion portion 44 formed in the fitting portion 41 of the finger grip 40 of the combined container-syringe body 10. By fitting the latch protrusion portion 44 into the engagement hole 58b, the latch protrusion portion 44 is engaged with the engagement plate 58 and is fixed thereto. When the engagement plate 58 is elastically deformed outward in the radial direction with the connection portion 58a serving as a fulcrum point, the latch protrusion portion 44 is separated from the engagement hole 58b, thereby releasing the engagement between the latch protrusion portion 44 and the engagement plate 58.

As shown in FIG. 1, the safety device 50 having the above-described structure is attached on the outer circumferential surface of the combined container-syringe body 10. In the combined container-syringe 1 shown in FIG. 1, the pressing ring 60 presses the return prevention stoppers 54 such that the return prevention stoppers 54 protrude inward in the radial direction.

In this case, the enlarged portion in the rear end side of the safety device 50 is positioned outside the fitting portion 41 of the finger grip 40 so as to form a gap between the enlarged portion and the fitting portion 41. The cylindrical coil spring 70 that can freely expand and contract in the axis O direction is housed within this gap in a compressed state so that the front end portion thereof abuts the spring receiving portion 52 formed on the inner circumferential surface of the safety device body 51 and the rear end portion thereof abuts the spring abutting stop portion 41a of the fitting portion 41 of the finger grip 40.

The latch protrusion portions 44, 44 of the finger grip 40 are fitted into the engagement holes 58b, 58b of the pair of the engagement plates 58, 58 of the safety device 50, respectively, such that the latch protrusion portions 44, 44 is engaged with the engagement plates 58, 58. Thereby, since the safety device 50 is fixed with respect to the finger grip 40, the coil spring 70 can be housed in a compressed state. Moreover, the movement of the safety device 50 due to the biasing force of the coil spring 70 can be prevented.

As described above, when the latch protrusion portions 44, 44 of the finger grip 40 are engaged with the engagement plates 58, 58 of the safety device 50, the safety device 50 covers the outer tube 20 and the rear end portion of the hub-luer lock 30 of the combined container-syringe body 10. A position of the safety device 50 in this state is the first position where the safety device 50 is separated from the injection needle 37 and the injection needle 37 is exposed. The engagement plate 58 and the latch protrusion portion 44 constitute the first retaining member that fixes the safety device 50 at the first position.

When the safety device 50 is positioned at the first position, the end portion of the engagement plate 58 of the safety device 50 extends so as to protrude backward than the flange surface 46 of the finger grip 40.

Figure 9:
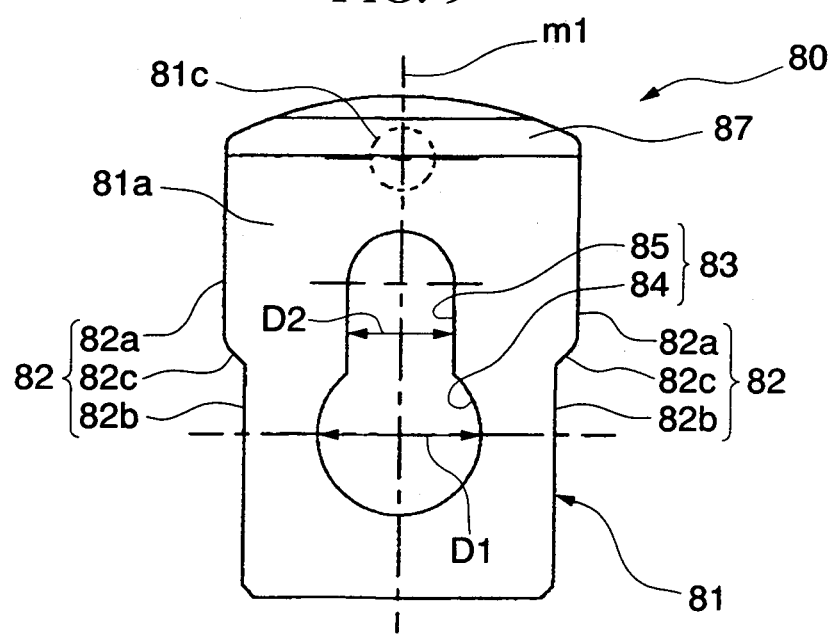
FIG. 9 is a view seen from arrow A in FIG. 8.
Figure 10:
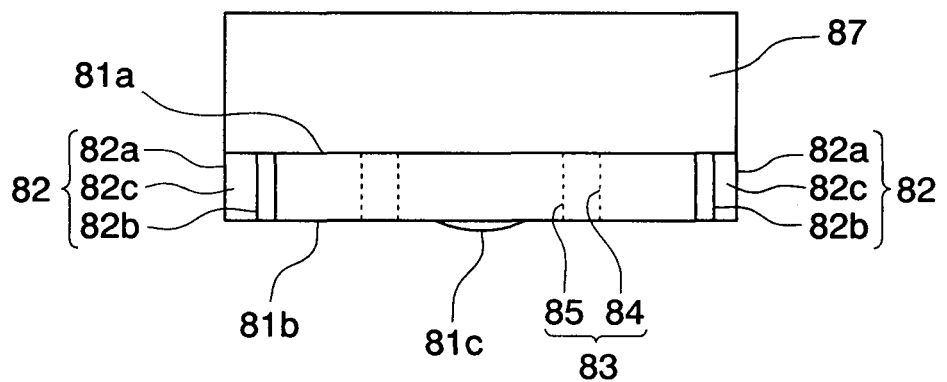
FIG. 10 is a view seen from arrow B in FIG. 8.

Next, the slide member (latch releasing member) 80 that releases the engagement of the safety device 50 by the first retaining member will be described. The slide member 80 is disposed on the flange surface 46 of the finger grip 40 in a freely sliding manner. The slide member 80 includes a slide plate 81 that has a substantially rectangular shape, and an operation plate 87 that protrudes vertically from a front surface 81a (a surface facing backward of the combined container-syringe 1) of the slide plate 81. As shown in FIG. 9, the slide member 80 is symmetry with respect to a line m1 when seen from the rear end.

The slide plate 81 has a substantially rectangular shape such that short sides of the slide plate 81 are parallel to the line m1, and long sides of the slide plate 81 are orthogonal to the line m1. The slide plate 81 further includes a rear surface 81b opposing to the front surface 81a. By the rear surface 81b making contact with the flange surface 46, the slide plate 81 slides on the flange surface 46. A slide plate latch portion 81c protruding in a hemispherical shape is formed on the rear surface 81, being positioned on the line m1 and in the vicinity of one end of the rear surface 81b in the longitudinal direction (that is, in upper side in FIG. 9). The slide plate latch portion 81c can be engaged with the latch recess portion 46a.

The distance in the line m1 direction between a pair of side surfaces 82, 82 of the slide plate 81 is shorter on the other end side (that is, on the lower side in FIG. 9) than on the one end side (that is, on the upper side). That is, the side surfaces 82, 82 include first side surfaces 82a, 82a positioned in the one end side and second side surfaces 82b, 82b positioned in the other end side, and the distance between the second side surfaces 82b, 82b is shorter than the distance between the first side surfaces 82a, 82a. The side surfaces 82, 82 further include sloping side surfaces 82c, 82c that connects the first side surfaces 82a, 82a and the second side surfaces 82b, 82b, respectively. The sloping side surfaces 82c, 82c slope such that they approach to each other toward the other end, that is, slope in the radial direction when the slide member 80 is disposed on the flange surface 46.

As shown in FIG. 9, a penetrating portion 83 that penetrates the slide plate 81 in the thickness direction thereof is formed at the center position of the slide plate 81 in a direction along the short side thereof, that is, on the line m1.

The penetrating portion 83 is disposed in the other end side in FIG. 9, and includes a larger-diameter hole 84 with an inner diameter of D1 and a smaller-diameter slit 85 that extends toward the one end from the larger-diameter hole 84 while maintaining an inner diameter (width) of D2. The inner diameter D2 of the smaller-diameter slit 85 is smaller than the inner diameter D1 of the larger-diameter hole 84.

The operation plate 87 is provided in the slide plate 81 at a position closer to the upper end than the penetrating portion 83. The operation plate 87 vertically protrudes from the front surface 81a and extends along the short side of the slide plate 81.

Figure 11:
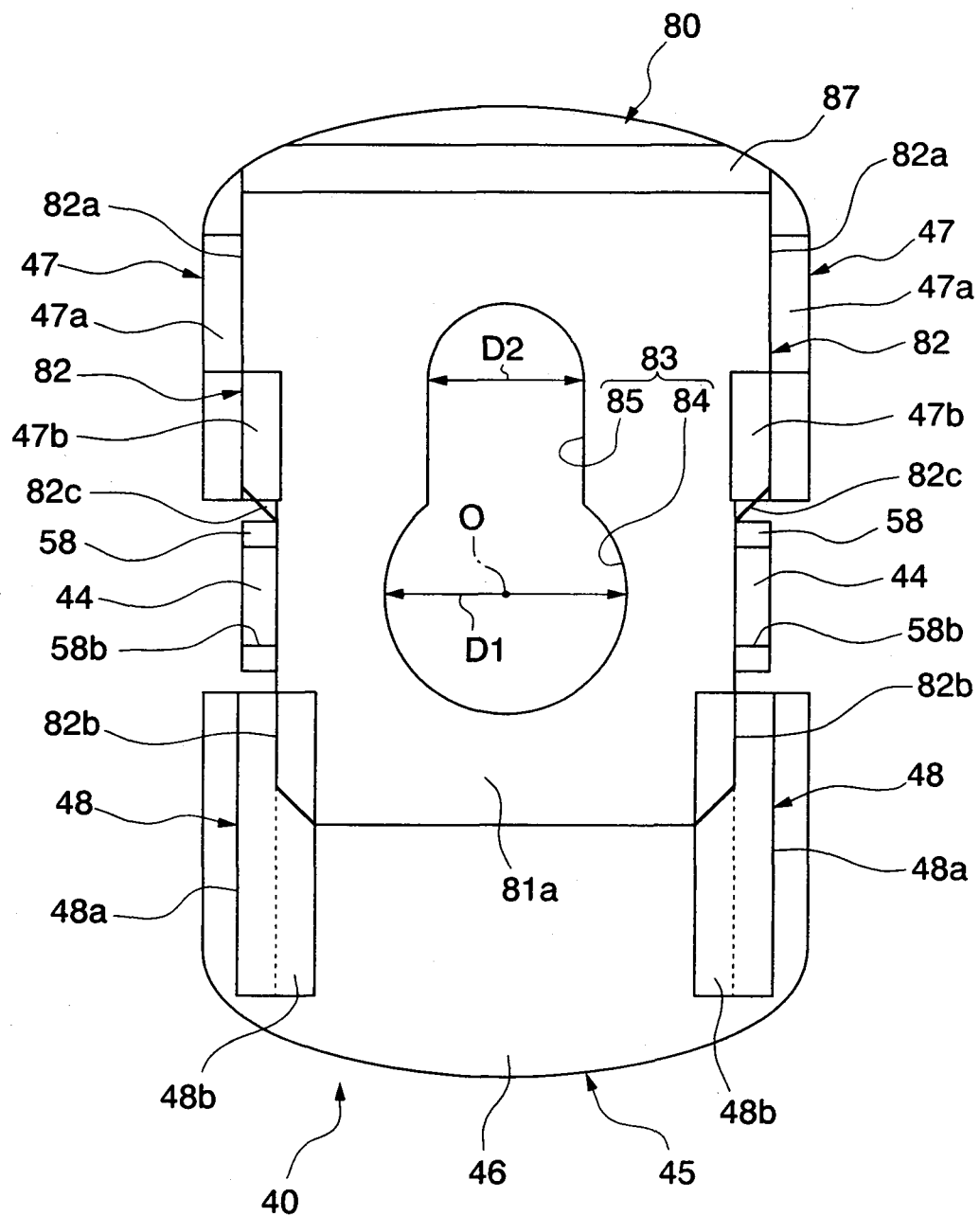
FIG. 11 is a view showing a state where the slide member is attached to the finger grip when the slide member is positioned at a waiting position.
Figure 12:
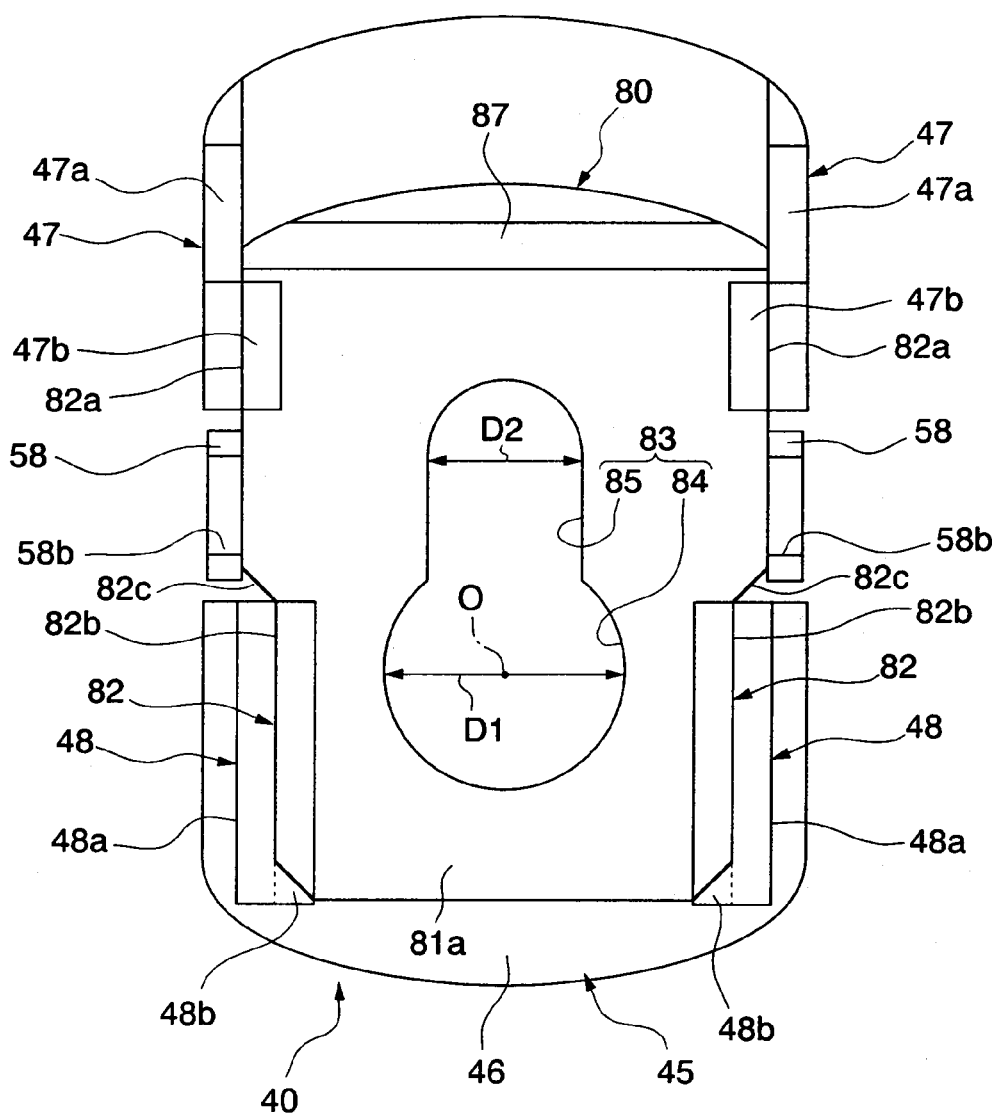
FIG. 12 is a view showing a state where the slide member is attached to the finger grip when the slide member is positioned at a releasing position.

FIGS. 11 and 12 show a state where the slide member 80 having the above-described structure is attached to the finger grip 40.

In FIG. 11, the slide member 80 is disposed in the one end side (that is, in the upper side) of the flange surface 46 and the rear surface 81b of the slide member 80 makes contact with the flange surface 46 of the flange portion 45. In this case, the pair of the first side surfaces 82a, 82a of the slide member 80 make contact with the side guides 47a, 47a of the first guide portions 47, 47 of the flange portion 45, respectively, and the pair of the second side surfaces 82b, 82b of the slide member 80 make contact with the side guides 48a, 48a of the second guide portions 48, 48, respectively.

Moreover, the first side surfaces 82a, 82a of the slide member 80 make contact with the inner surfaces of the engagement plates 58, 58 of safety device 50 at the first position, respectively. The center of the larger-diameter hole 84 of the penetrating portion 83 of the slide member 80 agrees with the axis O so that the larger diameter hole 84 connects to the insertion hole 43 (not shown in FIG. 11) in the rear end portion of the finger grip 40.

Thus, in FIG. 11, the slide member 80 is disposed in the upper side (that is, at a position closer to the outside in the radial direction of the combined container syringe 1) of the finger grip 40, the second side surfaces 82b, 82b makes contact with the engagement plates 58, 58, and the center of the larger-diameter hole 84 agrees with the axial O. Hereinafter, a position of the slide member 80 with respect to the finger grip 40 in this state is called "waiting position" of the slide member 80. At the waiting position, the slide member 80 is engaged with the flange surface 46 and is fixed thereto by fitting the slide plate latch portion 81c into the latch recess portion 46a of the flange surface 46.

In FIG. 12, the slide member 80 slides inward in the radial direction of the combined container-syringe 1 such that the slide member 80 is disposed in the lower side (that is, at a position closer to the inside in the radial direction of the combined container syringe 1) of the finger grip 40. In this case, the first side surfaces 82a, 82a of the slide member 80 make contact with the engagement plate 58, 58 and the axis O is positioned within the smaller-diameter slit 85. Hereinafter, a position of the slide member 80 with respect to the finger grip 40 in this state is called "releasing position" of the slide member 80. Furthermore, the direction to which the slide member 80 slides inward in the radial direction of the combined container-syringe 1 is called "sliding direction". In this state, the distance between the axis O and the end portion of the smaller-diameter slit 85 that is positioned in the uppermost side is half or more of the inner diameter D2 of the smaller-diameter slit 85.

In the combined container-syringe 1, a plunger rod 90 penetrates the penetrating portion 83 of the slide member 80 and the insertion hole 43 of the finger grip 40 from the rear end side and is inserted into the outer tube 20. The plunger rod 90 is provided in the rear end portion of the outer tube 20 and presses the stopper (not shown), which seals the drug solution from the rear end side in a liquid-tight manner, toward the front end.

Figure 13:
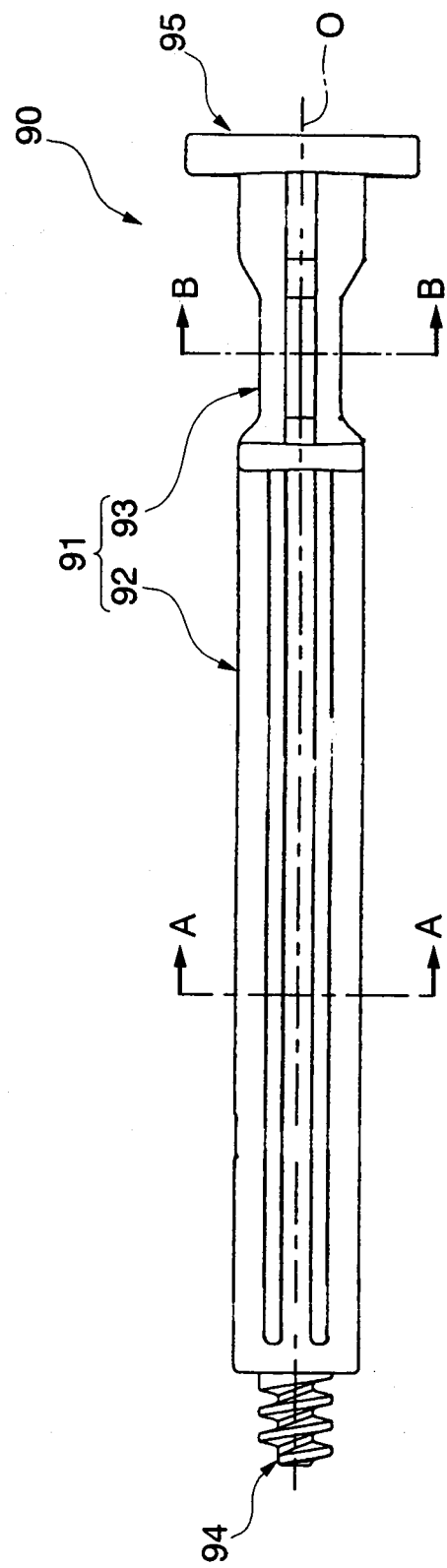
FIG. 13 is a side view of a plunger rod according to the embodiment of the invention.

As shown in FIG. 13, the plunger rod 90 includes a rod portion 91 that extends along the axis O. A screwed portion 94 that is screwed into the stopper is provided in the front end portion of the rod portion 91, and a pressing portion 95 that applies pressure to the stopper at the time of pressing the stopper is provided in the rear end portion of the rod portion 91.

The rod portion 91 includes a larger-diameter rod portion 92 and a smaller-diameter rod portion 93 having an outer diameter different from the larger-diameter rod portion 92.

Figure 14:
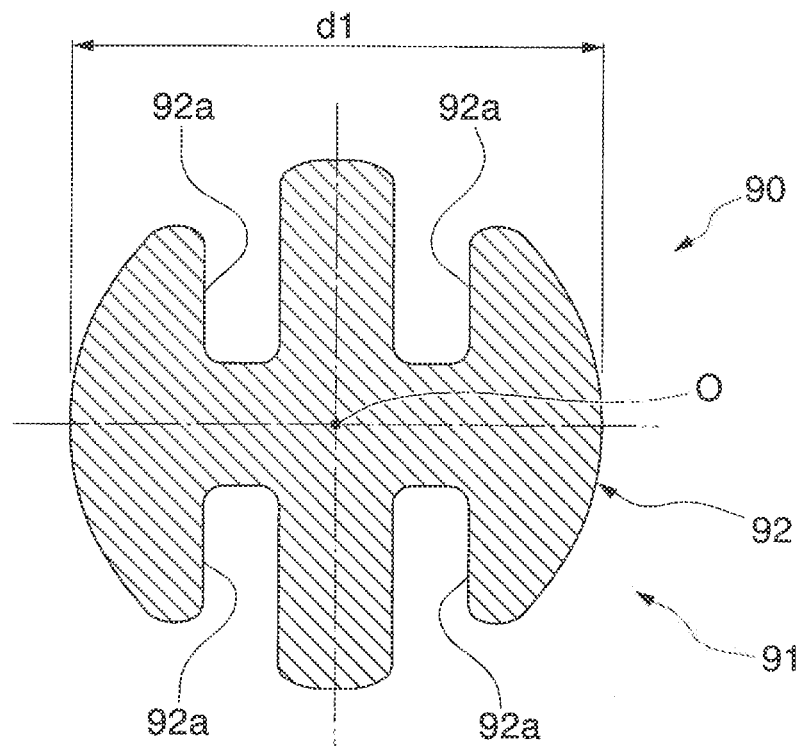
FIG. 14 is a cross-sectional view along the line A-A in FIG. 13.

As shown in FIG. 14, the larger-diameter rod portion 92 is formed such that a rod having a circular cross section with a diameter (outer diameter) of d1 is cut so as to form a plurality of pairs (two pairs in FIG. 14) of slits 92a that is parallel to the axis O. The slits 92a are parallel to each other and bottom surfaces of the pair of slits 92 faces to each other.

The outer diameter d1 of the larger-diameter rod portion 92 is equal to or slightly smaller than the inner diameter D1 of the larger-diameter hole 84, and is larger than the inner diameter D2 of the smaller-diameter slit 85. Thereby, the larger-diameter rod portion 92 can be inserted through the larger-diameter hole 84 of the penetrating portion 83, but cannot be inserted through the smaller-diameter slit 85.

Figure 15:
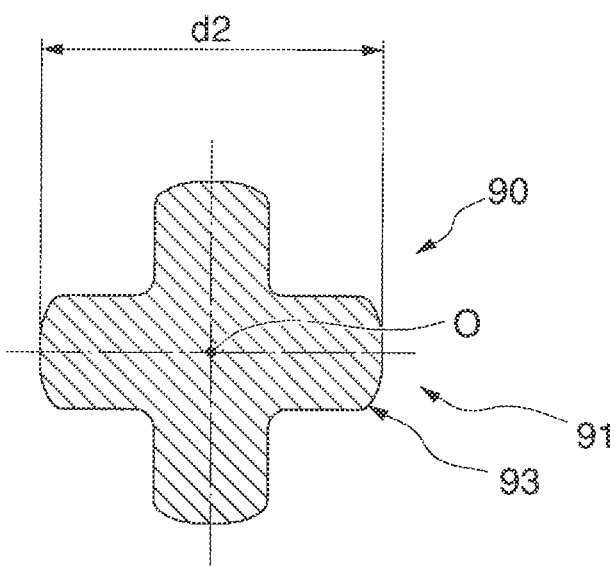
FIG. 15 is a cross-sectional view along the line B-B in FIG. 13.

As shown in FIG. 15, the smaller-diameter rod portion 93 has a substantially cross-shaped cross section such that a circle with a diameter (outer diameter) of d2 is cut in an L-shape at four portions uniformly spaced in the circumferential direction.

The outer diameter d2 of the smaller-diameter rod portion 93 is equal to or slightly smaller than the inner diameter D2 of the smaller-diameter slit 85 of the slide member 80. Thereby, the smaller-diameter rod portion 93 can be inserted through both the larger-diameter hole 84 and the smaller-diameter slit 85.

As shown in FIG. 13, in the rod portion 91, the larger-diameter rod 92 is disposed in the front end side and the smaller-diameter rod 93 is disposed in the rear end side. The length of the larger-diameter rod portion 92 in the axis O direction is sufficiently larger than the length of the smaller-diameter rod portion 93 in the axis O direction.

Before injection when the plunger rod 90 is pulled to the most rear end side, and at the time of injection when the plunger rod 90 is pushed forward to move the stopper forward, the larger-diameter rod portion 92 of the rod portion 91 is inserted through the larger-diameter hole 84 of the penetrating portion 83 of the slide member 80.

On the other hand, after the completion of injection when the plunger rod 90 is pushed to the most front end side, the smaller-diameter rod portion 93 of the rod portion 91 is inserted through the penetrating portion 83 of the slide member 80.

In the combined container-syringe 1 having the above-described structure, the injection needle 37 can be covered with the safety device 50 by sliding the slide member 80 after the completion of injection. Procedures thereof will be described hereinbelow.

Figure 16:
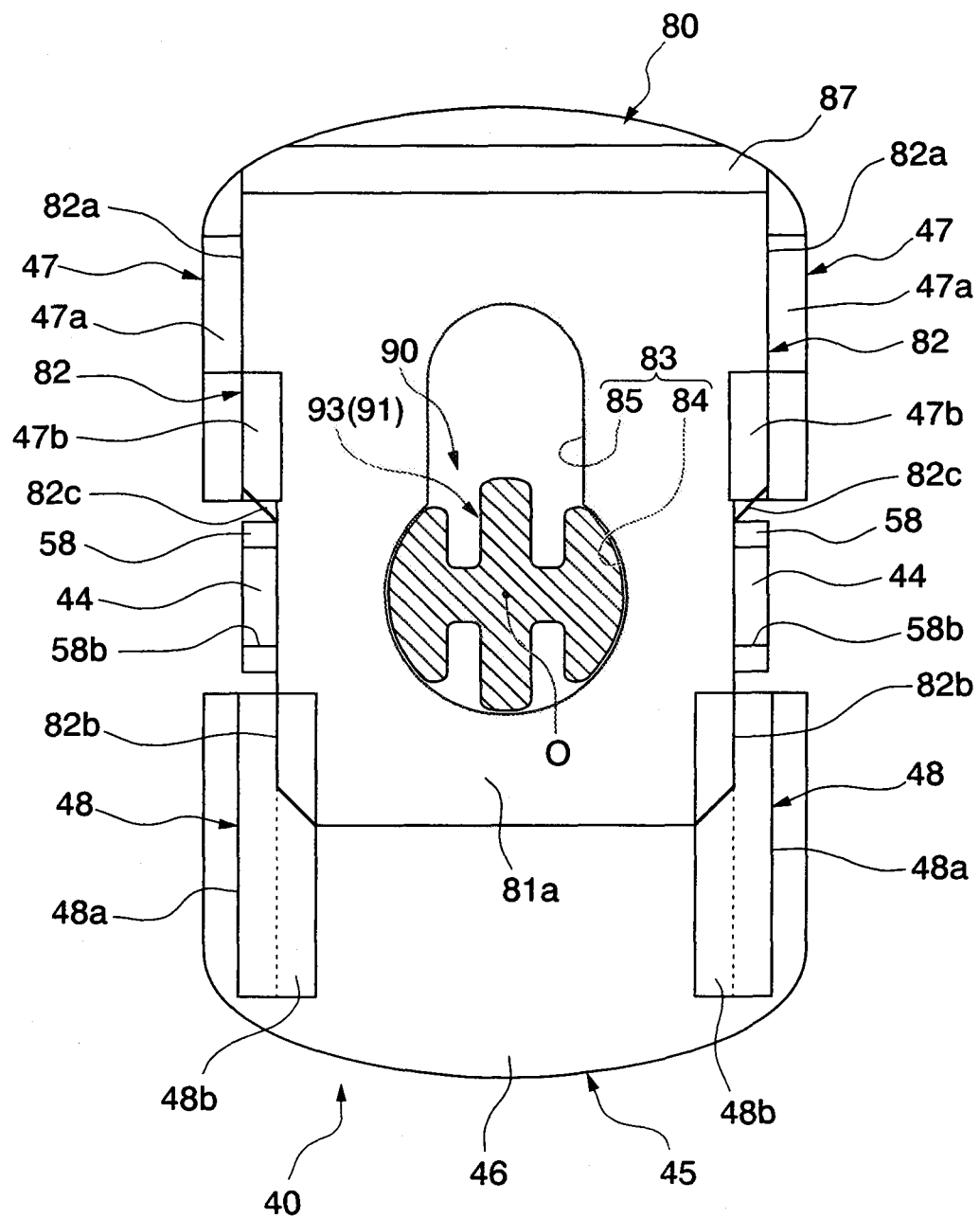
FIG. 16 is a rear view of the combined container-syringe according to the embodiment of the invention before and at the time of injection.

FIG. 16 is a view showing the finger grip 40 and the slide member 80 before injection when seen from the rear end. In this state, the slide member 80 is disposed at the waiting position, and the larger-diameter rod portion 92 of the plunger rod 90 is inserted through the larger-diameter hole 84 of the penetrating portion 83 of the slide member 80. The outer diameter d1 of the larger-diameter rod portion 92 of the plunger rod 90 is larger than the inner diameter D2 of the smaller-diameter slit 85. Therefore, even when a user attempts to slide the slide member 80 from the waiting position to the releasing position by pushing the operation plate 87 of the slide member 80 with his thumb or the like while holding the finger grip 40, since the larger-diameter rod portion 92 cannot be inserted through the smaller-diameter slit 85, the slide member 80 cannot be moved. Therefore, in this state, it is impossible to slide the slide member 80 to the releasing position.

Also at the time of injection when the plunger rod 90 is pressed and injection is made to a patient, since the larger-diameter rod portion 92 of the plunger rod 90 is inserted through the penetrating portion 83 of the slide member 80, it is impossible to slide the slide member 80 to the releasing position, similar to before injection.

Figure 17:
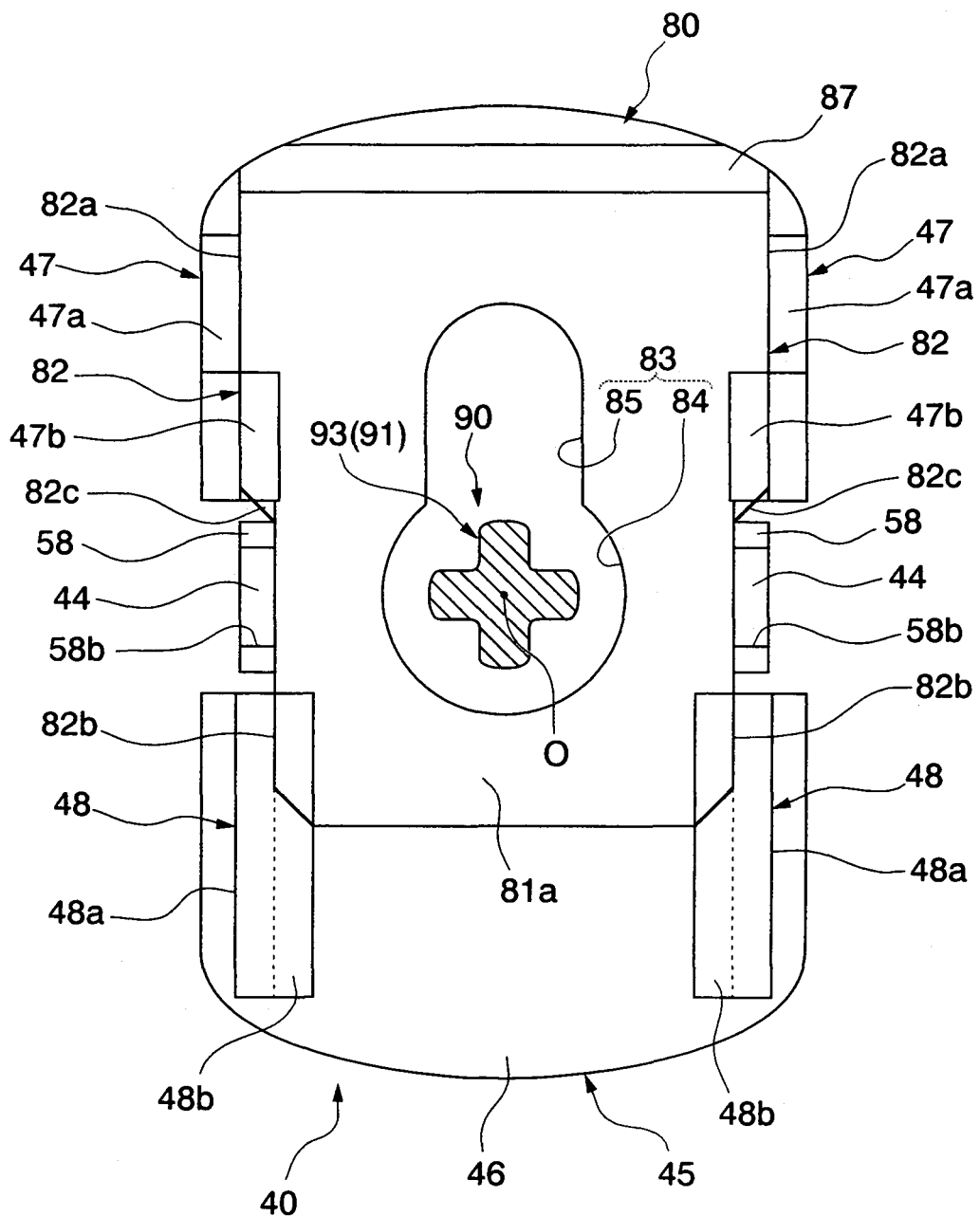
FIG. 17 is a rear view of the combined container-syringe according to the embodiment of the invention after the completion of injection.
Figure 18:
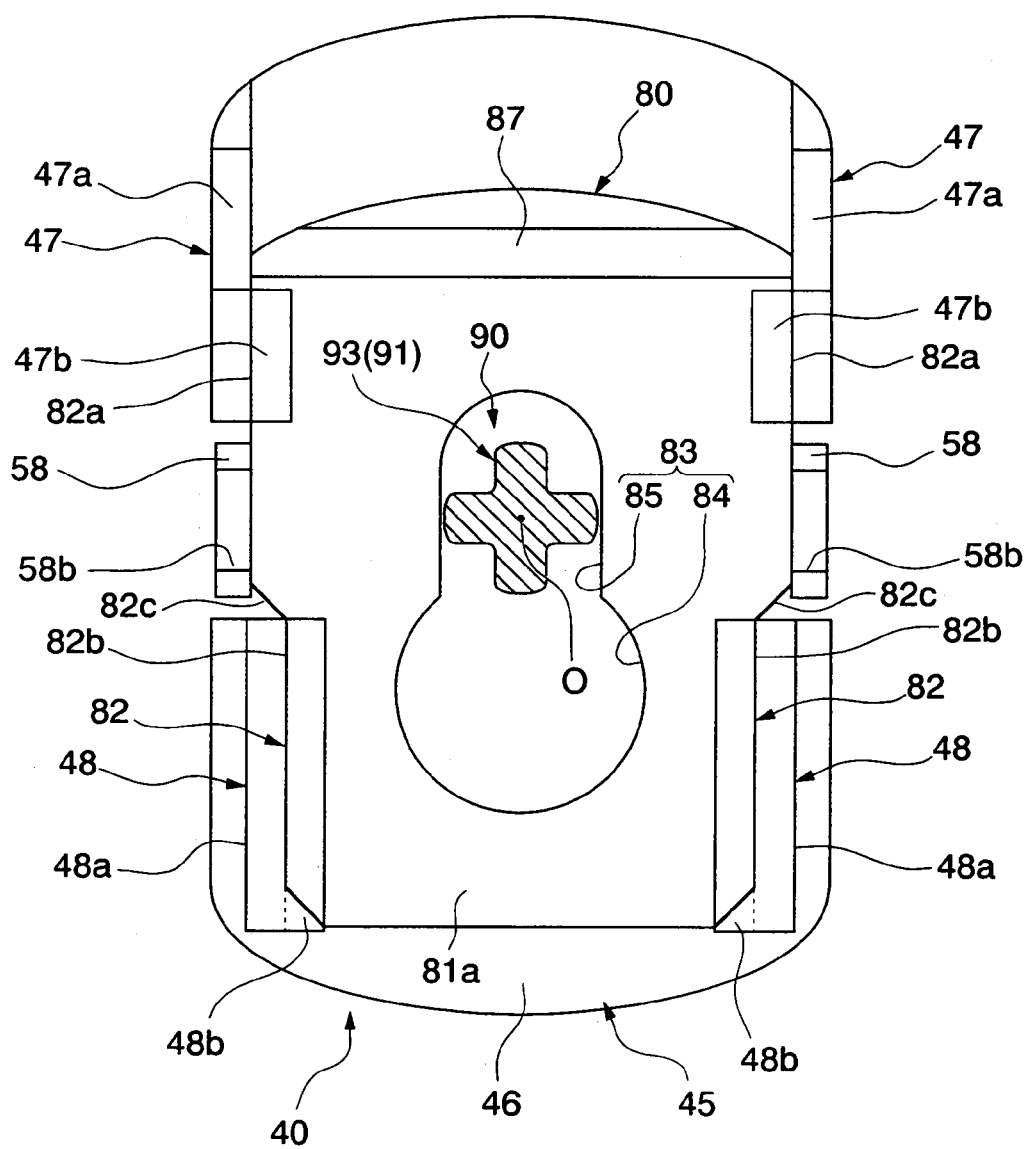
FIG. 18 is a rear view of the combined container-syringe according to the embodiment of the invention when the slide member moves from the waiting position to the releasing position.

After the completion of injection when the plunger rod 90 is completely pressed forward and injection to the patient is complete, as shown in FIG. 17, the smaller-diameter rod portion 93 of the plunger rod 90 is inserted through the penetrating portion 83 of the slide member 80. In this case, since the outer diameter d2 of the smaller-diameter rod portion 93 is smaller than the inner diameter D2 of the smaller-diameter slit 85, when sliding the slide member 80 to the sliding direction, the smaller-diameter rod portion 93 enters the smaller-diameter slit 85 from the larger-diameter hole 84 so that the smaller-diameter rod portion 93 is inserted through the smaller-diameter slit 85. Thereby, since the smaller-diameter rod portion 93 does not prevent the movement of the slide member 80, it is possible to slide the slide member 80 to the releasing position.

When the slide member 80 is positioned at the waiting position, as shown in FIG. 16, the engagement plates 58, 58 abut the second side surfaces 82b, 82b of the slide member 80. When the slide member 80 moves from the waiting position to the releasing position, as shown in FIG. 17, the engagement plates 58, 58 pass over the sloping side surfaces 82c, 82c and abut the first side surfaces 82a, 82a. That is, when passing over the sloping side surfaces 82c, 82c, the pair of engagement plates 58, 58 are elastically deformed outward in the radial direction so as to separate from each other, with the connection portions 58a serving as a fulcrum point.

Thereby, the engagement hole 58b of the engagement plate 58 disengages from the latch protrusion portion 44 of the finger grip 40 so that the engagement between the engagement plate 58 and the latch protrusion portion 44 (that is, the engagement by the first retaining member) is released.

When the engagement of the safety device 50 by the first retaining member is released thus, the safety device 50 moves toward the front end of the combined container-syringe body 10 by the biasing force of the coil spring 70. At this time, the sloping surface 54*b* of the return prevention stopper 54 abuts the rear engagement surface 31*b* of the device engagement portion 31, but the inner circumference surface of the safety device 50 expands so that the return prevention stopper 54 passes over the device engagement portion 31.

Figure 19:
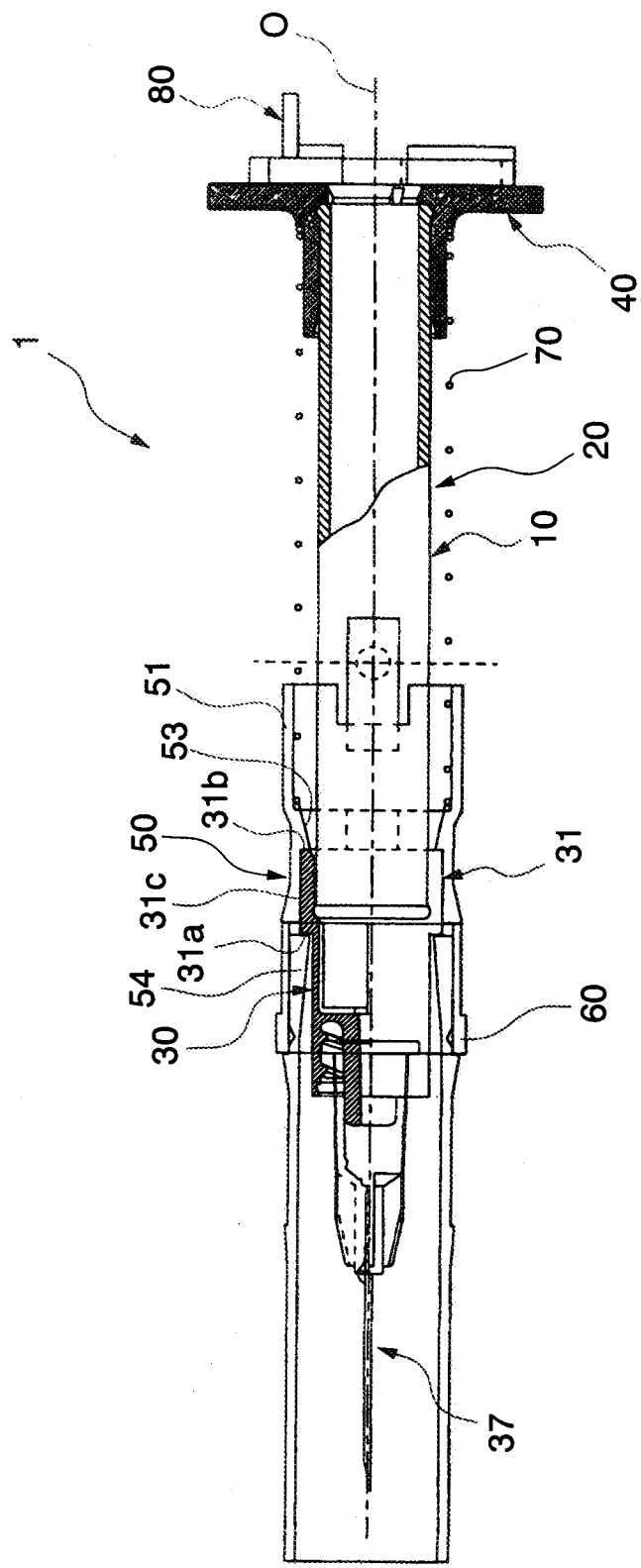
FIG. 19 is a side view showing a partial cross section of the combined container-syringe according to the embodiment of the invention in a state where the safety device covers an injection needle.

Afterward, as shown in FIG. 19, when the safety device 50 moves to the second position where the periphery of the injection needle 37 is completely covered with the safety device 50, the slip-out prevention stopper 53 and the rear engagement surface 31*b* of the device engagement portion 31 engage with each other, and further movement of the safety device 50 toward the front end is prevented. Moreover, in this state, even when attempting to move the safety device 50 toward the rear end, since the return prevention stopper 54 and the front engagement surface 31*a* of the device engagement portion 31 engage with each other, such movement is prevented. That is, the safety device 50 is fixed at the second position by the second retaining member that is constituted by the slip-out prevention stopper 53 and the return prevention stopper 54.

According to the combined container-syringe 1 described above, by moving the slide member 80 serving as the latch releasing member from the waiting position to the releasing position, the engagement of the safety device 50 at the first position by the first retaining member (the engagement plate 58 and the latch protrusion portion 44) is released. Thereby, since the safety device 50 moves to the second position where the safety device 50 covers the injection needle 37, it is possible to easily and reliably covers the injection needle 37 with the safety device 50. Therefore, handleability and safety of the combined container-syringe 1 are improved.

Moreover, it is possible to move the slide member 50 forward only with one hand by holding the finger grip 40 by one hand and performing the moving operation of the slide member 80 with thumb of the one hand. Therefore, the handleability of the combined container-syringe 1 is further improved.

Moreover, when moving the slide member 80 from the waiting position to the releasing position, since the sloping side surface 82*c* of the slide member 80 presses the engagement plate 58 of the safety device 50 outward in the radial direction, it is possible to easily and reliably release the engagement of the safety device 50 by the first retaining member constituted by the engagement plate 58 and the latch protrusion portion 44.

Moreover, before and at the time of injection, movement of the slide member 80 is prevented by the larger-diameter rod portion 92 of the plunger rod 90. On the other hand, after the completion of injection, since the smaller-diameter rod portion 93 of the plunger rod 90 is inserted through the penetrating portion 83 of the slide member 80, movement of the slide member 80 is allowed.

Therefore, it is possible to slide the slide member 80 from the waiting position to the releasing position only after the completion of injection, and it is possible to reliably prevent accidental movement of the safety device 50 before and at the time of injection.

Moreover, once the injection needle 37 is covered with the safety device 50, the device engagement portion 31 is fixed on front end side and rear end side by the slip-out prevention stopper 53 and the return prevention stopper 54. That is, the safety device 50 can be reliably fixed at the second position by the second retaining member that is constituted by the slip-out prevention stopper 53 and the return prevention stopper 54. As a result, the safety device 50 does not separate from the combined container-syringe body 10 as a result of proceeding too far to the front end side, and neither does it move in the direction of the rear end and cause the injection needle 37 to be exposed.

Moreover, since the return prevention stopper 54 protrudes inward in the radial direction only when pressed by the pressing ring 60, it is possible to easily mount the safety device 50 on the combined container-syringe body 10 and then fix the safety device 50 at the position where the safety device 50 covers the injection needle 37.

That is, when the safety device 50 is mounted on the outer circumferential surface of the combined container-syringe body 10 from the front end side, since the sloping surface 53*a* of the slip-out prevention stopper 53 abuts the front engagement surface 31*a* and the inner circumferential surface of the safety device 50 is flexed, the slip-out prevention stopper 53 easily passes over the device engagement portion 31. In this case, since it is possible to prevent the return prevention stoppers 54 from protruding inward in the radial direction, the return prevention stoppers 54 do not abut the device engagement portion 31. Therefore, even though the slip-out prevention stopper 53 and the return prevention stopper 54 are provided in the safety device 50, it is possible to easily mount the safety device 50.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, although the combined container-syringe 1 of this embodiment is a single chamber combined container-syringe, the present invention is not limited to a single chamber combined container-syringe, and it of course may also be applied to a dual chamber combined container-syringe.

What is claimed is:

1. A combined container-syringe comprising:
   a combined container-syringe body that has an outer tube inside of which a drug solution is filled, a cylindrical tip which is attached to a front end portion of the outer tube and to a front end portion of which an injection needle is attached, and a finger grip that is attached to a rear end portion of the outer tube;
   a cylindrical safety device which is attached on an outer circumferential surface of the outer tube in a freely sliding manner;
   a first retaining member that fixes the safety device in a disengageable manner at a first position where the safety device is separated from the injection needle;
   a second retaining member that fixes the safety device at a second position where the safety device covers the injection needle;
   a biasing member that biases the safety device in the direction from the first position to the second position; and
   a latch releasing member that releases the engagement by the first retaining member, wherein the finger grip has a cylindrical fitting portion that is attached to the rear end portion of the outer tube, and a flange surface that protrudes outward in a radial direction of the combined container-syringe body from an outer circumferential surface of a rear end portion of the fitting portion and faces backward;

the first retaining member has an engagement portion that is provided in a rear end portion of the safety device and a latch portion that is provided on the outer circumferential surface of the fitting portion and is engaged with the engagement portion;

the latch releasing member is a slide member that is capable of sliding on the flange surface along the radial direction of the combined container-syringe body from a waiting position where the slide member is disposed at a position closer to the outside in the radial direction of the combined container-syringe body to a releasing position where the slide member is disposed at a position closer to the inside in the radial direction of the combined container-syringe body;

the slide member releases the engagement of the latch portion with the engagement portion when the slide member slides from the waiting position to the releasing position;

the engagement portion protrudes parallel to an axis of the combined container-syringe body from the rear end portion of the safety device and is elastically deformable in the radial direction of the combined container-syringe body;

the slide member has a sloping side surface that slopes inward in the radial direction of the combined container-syringe body from the waiting position side to the releasing position side and is capable of abutting an inner surface of the engagement portion;

the sloping side surface presses the engagement portion such that the engagement portion is elastically deformed outward in the radial direction of the combined container-syringe body when the slide member moves to the releasing position;

the combined container-syringe further comprising:

a plunger rod which extends along the axis of the combined container-syringe body, is inserted into the outer tube from the rear end side, and is pushed forward at the time of injection, wherein the slide member has a penetrating portion having a larger-diameter hole that penetrates the slide member along the axis when the slide member is positioned at the waiting position, and a smaller-diameter slit that penetrates the slide member along the axis when the slide member is positioned at the waiting position, extends along a direction to which the sliding member slides, and is connected with the larger-diameter hole;

the plunger rod comprises:

a larger-diameter rod portion that is capable of being inserted into the larger-diameter hole but is not capable of being inserted into the smaller-diameter slit, and a smaller-diameter rod portion that is capable of being inserted into the larger-diameter hole and the smaller-diameter slit;

the larger-diameter rod portion is inserted through the penetrating portion before injection when the plunger rod is positioned at the most rear end side and at the time of injection when the plunger rod is pushed forward; and the smaller-diameter rod portion is inserted through the penetrating portion after completion of injection when the plunger rod is pushed to the front-most end side.

2. The combined container-syringe according to claim 1, wherein the second retaining member has a device engagement portion that is formed by a part of the cylindrical tip expanding in diameter, and has a front engagement surface facing forward and a rear engagement surface facing backward;

a return prevention stopper that protrudes from an inner circumferential surface of the safety device, and is engaged with the front engagement surface when the safety device is positioned at the second position so as to prevent movement of the safety device toward the rear end; and a slip-out prevention stopper that protrudes from the inner circumferential surface of the safety device at a position closer to the rear end than the slip-out prevention stopper, and is engaged with the rear engagement surface when the safety device is positioned at the second position so as to prevent movement of the safety device toward the front end.

3. The combined container-syringe according to claim 2, wherein the return prevention stopper slopes inward in the radial direction of the combined container-syringe body toward the rear end and the slip-out prevention stopper slopes inward in the radial direction of the combined container-syringe body toward the front end.

4. The combined container-syringe according to claim 2, wherein the slip-out prevention stopper slopes inward in the radial direction of the combined container-syringe body toward the front end;

wherein the return prevention stopper is elastically deformable in the radial direction of the combined container-syringe body;

wherein a pressing ring is fitted on an outer circumferential surface of the safety device in a freely sliding manner; and wherein the return prevention stopper protrudes from the inner circumferential surface of the safety device by sliding the pressing ring to the position of the return prevention stopper such that the pressing ring presses the return prevention stopper inward in the radial direction of the combined container-syringe body.

5. The combined container-syringe according to claim 1, wherein the safety device has a spring receiving portion that is formed on the inner circumferential surface of the rear end portion thereof;

wherein the biasing member is a coil spring; and wherein, in a state of the safety device being fixed at the first position, the coil spring is mounted in a compressed state between the spring receiving portion and the finger grip.

* * * * *